US005660979A

United States Patent [19]
Romano et al.

[11] Patent Number: 5,660,979
[45] Date of Patent: Aug. 26, 1997

[54] DETECTION OF HUMAN RETROVIRUS INFECTION

[75] Inventors: Joseph W. Romano, Derwood; Ranajit Pal, Gaithersburg, both of Md.

[73] Assignee: Akzo Nobel N.V., Arnhem, Netherlands

[21] Appl. No.: 334,499

[22] Filed: Nov. 4, 1994

[51] Int. Cl.$^6$ .............................. C12Q 1/70; C12Q 1/68; C12P 19/34; C07H 21/04
[52] U.S. Cl. ..................... 435/5; 435/6; 435/91.2; 536/24.3; 536/24.32
[58] Field of Search ..................... 435/5, 6, 91.2, 435/235.1, 238; 536/24.3

[56] References Cited

U.S. PATENT DOCUMENTS 5,118,605  6/1992  Urdea et al. ......................... 435/6

FOREIGN PATENT DOCUMENTS

| A 0569272 | 11/1993 | European Pat. Off. |
| WOA9323574 | 11/1993 | WIPO |
| WOA9400598 | 1/1994 | WIPO |
| WOA19491 | 9/1994 | WIPO |

OTHER PUBLICATIONS

Furtado et al, Analysis of Alternatively Spliced Human Immunodeficiency Virus Type-1 mRNA Species, One of Which Encodes a Novel TATENV Fusion Protein, Virology 185:258–270, 1991.
Smith et al, J. of General Virology 73:1825–1828, 1992.
Peng and Haase, Annu Conf. Australias Soc, HIV Med, 5, p. 109, 1993, meeting abstract.
Lewis et al., Prog. Med. Virol., 40:19–47, 1993.
Meylan et al., Virology, 193:138–148, 1993.
M. Arens et al., "Alterations in Spliced nd Unspliced HIV–1 Specific RNA Detection in Peripheral Blood Mononuclear Cells of Individuals with Varying CD4–Positive Lymphocyte Counts," Aids Research and Human Retroviruses, 9:12:1257–1263, 1993.
R. Boom et al., "Rapid and Simple Method for Purification of Nucleic Acids," Journal of Clinical Microbiology, 28:3:495–503, Mar. 1990.
R. Balachandran et al., "Human Immunodeficiency Viirus Isolates from Asymptomatic Homosexual Men and from AIDS Patients Have Distinct Biologic and Genetic Properties," Virology, 180:229–238 (1991).
D.J. Capon et al., "The CD4–gp120 Interaction and AIDS Pathogens," Ann. Rev. Immun., vol. 9: pp. 649–678, 1991.
D.S. Dimitrov et al., "Quantitation of Human Immunodeficiency Virus Type 1 Infection Kinetics," Journal of Virology, 67:4:2182–2190, Apr. 1993.
E.M. Fenyo et al., "Distinct Replicative and Cytopathic Characteristics of Human Immunodeficiency Virus Isolates" Journal of Virology, 62:11:4414–4419, Nov. 1988.
M.A. Fischl et al., "The Efficacy of Azidothymidine (AZT) in the Treatment of Patients with AIDS and AIDS–Related Complex," The New England Journal of Medicine, 317:4:185–191, Jul. 23, 1987.
T. Kievits et al., "NASBA isothermal enzymatic in vitro nucleic acid amplification optimized for the diagnosis of HIV–1 infection," Journal of Virological Methods, 35:273–286, 1991.
S. Laal et al., "A Rapid, Automated Microtiter Assay for Measuring Neutralization of HIV–1," AIDS Research and Human Retroviruses, 9:781–785, 1993.

(List continued on next page.)

Primary Examiner—W. Gary Jones
Assistant Examiner—Dianne Rees
Attorney, Agent, or Firm—William M. Blackstone; Mary E. Gormley

[57] ABSTRACT

A method for determining virus replication in human cells by human retrovirus using RNA amplification comprising detecting the hybridization of an RNA probe which specifically hybridizes with spliced RNA and not with genomic RNA. This method permits early detection of RNA replication resulting from primary infection without detecting non-replicating virus.

8 Claims, 4 Drawing Sheets

OTHER PUBLICATIONS

T.J. Matthews et al., "Restricted neutralization of divergent human T–lymphotropic virus type III isolates by antibodies to the major envelope glycoprotein," *Proc. Natl. Acad. Sci., USA*, 83:9709–9713, Dec. 1986.

P.L. Nara et al., "Simple, Rapid, Quantatative, Syncytium–Forming Microassay for the Detection of Human Immunodeficiency Virus Neutralizing Antibody," *AIDS Research and Human Retroviruses*, 3:3:283–302, 1987.

R. Pal et al., "Characterization of a Neutralizing Monoclonal Antibody to the External Glycoprotein of HIV–1," *Intervirology*, 86:86–93, 1992.

M.L. Robb et al., "HIV Neutralization Assay Using Polymerase Chain Reaction–Derived Molecular Signals," *Journal of Aquired Immune Deficiency Syndromes* 5:1224–1229, 1992.

M. Robert–Guroff et al., "HTLV–III–neutralizing antibodies in patients with AIDS and AIDS–related complex," *Nature*, 316:72–74, Jul. 4, 1985.

Z.F. Rosenberg et al., "Immunopathogenesis of HIV Infection," *The FASEB Journal*, 5:2382–2390, Jul. 1991.

K. Saksela et al., "Human immunodeficiency virus type 1 mRNA expression in peripheral blood cells predicts disease progression independently of the numbers of CD4+lymphocytes," *Proc. Natl. Acad. Sci., USA*, 91:1104–1108, Feb. 1994.

H. Schuitemaker et al., "Monocytotropic Human Immunodeficiency Virus Type 1 (HIV–1) Variants Detectable in all stages of HIV–1 Infection Lack T–Cell Line Tropism and Syncytium–Inducing Ability in Primary T–Cell Culture," *Journal of Virology*, 65:1:356–363, Jan. 1991.

B. van Gemen et al., "Quantification of HIV–1RNA in plasma using NASBA during HIV–1 primary infection," *Virological Mehtods*, 43:177–188, 1993.

M. Tersmette et al., "Differential Syncytium–Inducing Capacity of Human Immunodeficiency Virus Isolates: Frequent Detection of Syncytim–Inducing Isolates in Patients with Acquired Immunodeficiency Syndrome (AIDS) and AIDS–Related Complex," *Journal of Virology*, 62:6:2026–2032, Jun. 1988.

B. van Gemen et al., "A one–tube quantitative HIV–1 RNA NASBA nucleic acid amplification assay using electrochemiluminescent (ECL) labeled probes," *Journal of Virological Methods*, 49:157–168, 1994.

L. Ratner, "Molecular biology and pathogenesis of HIV infection," *Current Opinion in Infectious Diseases*, 6:181–190, 1993.

C. Cheng–Mayer, "Biological and molecular features of HIV–1 related to tissue tropism," *AIDS*, 4 (Sup. 1):540–556.

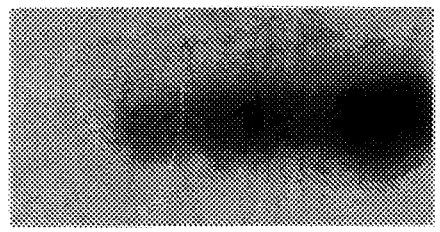
FIG. IA
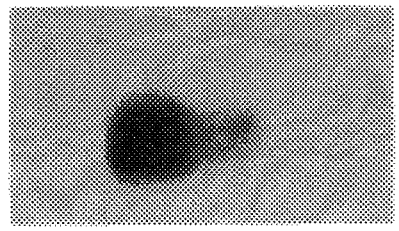
FIG. IB
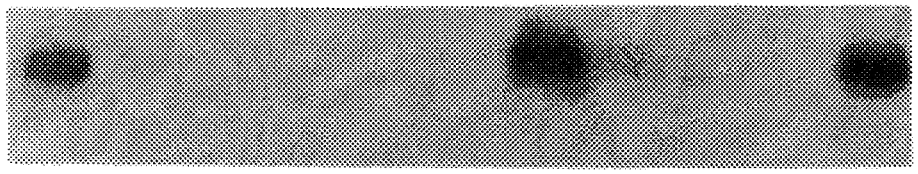
FIG. 2A
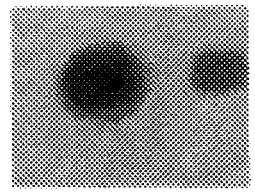
FIG. 2B

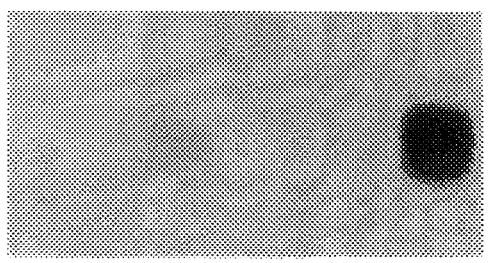
FIG. 3A
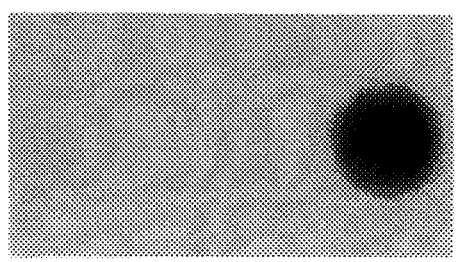
FIG. 3B
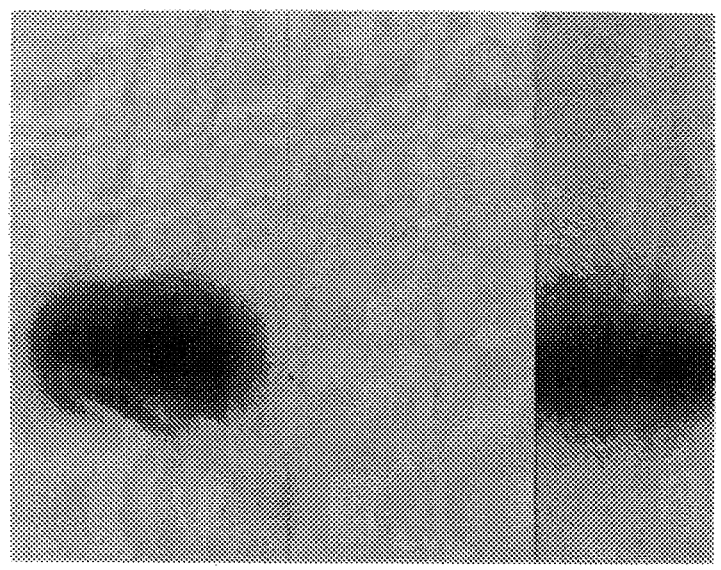
FIG. 4

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "DNA Primer"

( i i i ) HYPOTHETICAL: NO ( i v ) ANTI-SENSE: YES ( i x ) FEATURE:
  ( A ) NAME/KEY: misc_feature
  ( B ) LOCATION: 1..25
  ( D ) OTHER INFORMATION: /function="T7 RNA polymerase
    promoter"

( x i ) SEQUENCE DESCRIPTION: SEQ ID NO:1:

AATTCTAATA CGACTCACTA TAGGGATTGC CTCTCTGCAT CATTA     45

( 2 ) INFORMATION FOR SEQ ID NO:2:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: Not Relevant ( i i ) MOLECULE TYPE: other nucleic acid
  ( A ) DESCRIPTION: /desc = "DNA primer"

( i i i ) HYPOTHETICAL: NO ( i v ) ANTI-SENSE: YES ( x i ) SEQUENCE DESCRIPTION: SEQ ID NO:2:

AGCATTGGGA CCAGCGGCTA     20

( 2 ) INFORMATION FOR SEQ ID NO:3:

( i ) SEQUENCE CHARACTERISTICS:
  ( A ) LENGTH: 51 base pairs
  ( B ) TYPE: nucleic acid
  ( C ) STRANDEDNESS: single
  ( D ) TOPOLOGY: Not Relevant ( i i ) MOLECULE TYPE: other nucleic acid
  ( A ) DESCRIPTION: /desc = "DNA primer"

( i i i ) HYPOTHETICAL: NO ( i v ) ANTI-SENSE: YES ( i x ) FEATURE:
  ( A ) NAME/KEY: misc_feature
  ( B ) LOCATION: 1..25
  ( D ) OTHER INFORMATION: /function="T7 RNA polymerase
    promoter"

( x i ) SEQUENCE DESCRIPTION: SEQ ID NO:3:

AATTCTAATA CGACTCACTA TAGGGCCAAG GATCCGTTCA CTAATCGAAT G     51

( 2 ) INFORMATION FOR SEQ ID NO:4:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: Not Relevant ( i i ) MOLECULE TYPE: other nucleic acid
  ( A ) DESCRIPTION: /desc = "DNA primer"

( i i i ) HYPOTHETICAL: NO ( i v ) ANTI-SENSE: YES ( x i ) SEQUENCE DESCRIPTION: SEQ ID NO:4:

TCAGAACAGT CAGACTCATC AAGCTTC     27

( 2 ) INFORMATION FOR SEQ ID NO:5:

(i) SEQUENCE CHARACTERISTICS:
    (A) LENGTH: 29 base pairs
    (B) TYPE: nucleic acid
    (C) STRANDEDNESS: single
    (D) TOPOLOGY: Not Relevant (ii) MOLECULE TYPE: other nucleic acid
    (A) DESCRIPTION: /desc = "DNA probe"

(iii) HYPOTHETICAL: NO (iv) ANTI-SENSE: YES (xi) SEQUENCE DESCRIPTION: SEQ ID NO:5:

TAGAAGAAAT GATGACAGCA TGTCAGTGA    29

(2) INFORMATION FOR SEQ ID NO:6:

(i) SEQUENCE CHARACTERISTICS:
    (A) LENGTH: 24 base pairs
    (B) TYPE: nucleic acid
    (C) STRANDEDNESS: single
    (D) TOPOLOGY: Not Relevant (ii) MOLECULE TYPE: other nucleic acid
    (A) DESCRIPTION: /desc = "DNA probe"

(iii) HYPOTHETICAL: NO (iv) ANTI-SENSE: YES (xi) SEQUENCE DESCRIPTION: SEQ ID NO:6:

TCTATCAAAG CAACCCACCT CCCA    24

DETECTION OF HUMAN RETROVIRUS INFECTION

DESCRIPTION OF THE INVENTION

This invention relates to a method for assaying human retrovirus infection of cells by detecting virus replication at an early time point. We detect spliced mRNA coding for regulatory proteins necessary for the replication of the virus. Only replicating virus produce spliced mRNA and thus this assay is specific for infective virus. Our method uses known RNA amplification techniques for amplifying RNA and a probe which hybridizes with the junction of the spliced RNA.

BACKGROUND OF THE INVENTION

Infection of CD4-positive lymphocytes by Human Immunodeficiency Virus (HIV-1) involves a complex pathway. This is also true for infection by other retroviruses. To chart the course of HIV-1 infection, as an example, it is absolutely necessary to have a sensitive biologically relevant infectivity assay that determines primary infection. Such an assay is also critical for the valid evaluation of neutralization or inhibition by antibodies or antiviral agents. Infection of target cells by HIV-1, for example, can be detected by several methods, including observation of virus induced cytopathic effects, such as syncytia formation; immunofluorescence assays to detect expression of vital antigens; antigen capture assays that detect the release of viral proteins, such as p24; and detection of reverse transcriptase activity in the supernatants of infected cells. Unfortunately, although these assays are sensitive for the detection of infection of neoplastic T-cell lines, they are of little use when peripheral blood mononuclear cells (PBMC) are used as the target cells, particularly when the assays are employed at a very early time. This is because, typically, a very low percentage of the cells are infected under in-vitro conditions by primary HIV-1 isolates. Infection must be allowed to progress for an extended period of time (usually a minimum of six days) before it can be detected by conventional methods. Further, many HIV-1 isolates infect PBMC without inducing syncytia formation. Thus, the applicability of these conventional assays for the detection of infection by HIV-1 is somewhat limited.

The major objective of the present invention was the development of a sensitive infection assay, which would allow for the accurate study of the human retrovirus infection process and would also permit valid evaluation of potentially therapeutic antiviral agents. Therefore, we tried the molecular amplification technique known as NASBA (Kievits et al., 1991), which has proven to be a particularly effective and sensitive means of amplification for detecting the RNA genome of HIV-1.

NASBA is an isothermal method of specific amplification that relies on a set of two primers specific for the target sequence. The antisense primer (P1) has a 5' overhang that encodes the T7 RNA polymerase promoter; the sense primer (P2) is specific for a region upstream of the P1 annealing site. During the early stages of the reaction, a cDNA copy of the target area is generated through the coordinated activities of reverse transcriptase and RNase H. The resulting cDNA encodes a functional T7 RNA polymerase promoter at one end. Amplification can therefore occur through the action of the T7 RNA polymerase. The final NASBA product consists of single stranded copies of antisense RNA representing the area targeted by the primers.

We have found NASBA to be useful as an endpoint assay for the detection of infection of PBMC and CEM50 (CEM) cells by HIV-1. We used the assay to detect both HIV-1 genomic RNA and spliced HIV-1 mRNA transcript target sequences resulting from primary infection, with little contribution from secondary infection.

SUMMARY OF THE INVENTION

This invention relates to a method for assaying infection of cells by human retroviruses. Primary infection is signaled by the detection of spliced mRNA coding for regulatory proteins necessary for the replication of the virus. Our method uses known RNA amplification techniques for amplifying RNA and a probe specific for the junction of the spliced RNA.

The method of the invention is useful for testing the efficacy of antiviral drugs. Through RNA amplification and probe detection of the spliced junction, primary infection of peripheral blood mononuclear cells can be detected.

DESCRIPTION OF THE DRAWINGS

FIG. 1 illustrates preliminary optimization of NASBA as an infectivity end point assay.

Figure 5A:
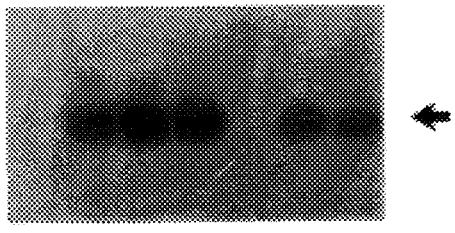

A. PHA-stimulated PBMC were infected with 1.0 (lane 2), 2.0 (lane 3), 4.0 (lane 4) and 16.0 (lane 5) $TCID_{50}$ of HIV-$1_{IIIB}$. After 3 days, nucleic acids were extracted from 100 µl of the cultures. Samples were then amplified by NASBA using the gag region primer set and the resulting amplification products were resolved in an agarose gel, vacuum transferred to a nylon membrane, hybridized with a $^{32}P$ labeled probe, and exposed to film in autoradiography.

B. PHA stimulated PBMC were infected with 4 $TCID_{50}$ of HIV-$1_{IIIB}$ and were analyzed by NASBA as described in A. at 0 hr. (lane 5), 24 hr. (lane 4), 48 hr. (lane 3), and 72 hr (lane 2). Lane 1 in A. and B. is a medium only (i.e., no cells).

FIG. 2 illustrates NASBA as an end point assay for the titration of antibody neutralization of HIV-1 infection of PBMC.

A. Four $TCID_{50}$ of HIV-$1_{IIIB}$ were pretreated for 60 min. on ice with 1:2000 (lane 1), 1:200 (lane 2), 1:20 (lane 3) dilutions of M77 monoclonal antibody (monoclonal antibody specific for V3 loop of gp120 or HIV-$1_{IIIB}$, available from Advance BioScience Laboratories, Kensington, Md.), or 1:2000 (lane 5), 1:200 (lane 6), 1:20 (lane 7), dilutions of neutralizing patient serum PS12 (HIV-1 infected human serum available commercially), or with medium only (lane 8). PHA-stimulated PBMC were then infected with the antibody-treated virus for 60 min. at 37° C. After 3 days, cultures were analyzed by NASBA using the gag region primer set as in FIG. 1. Lane 4 is a medium only control.

B. Four $TCID_{50}$ of HIV-$1_{IIIB}$ were pretreated with either 1:20 dilution of normal human serum (lane 2), 1:20 dilution of PS12 (lane 3), or medium only (lane 4), and were used to infect PBMC as previously described. After 3 days, the cultures were analyzed by NASBA with the gag region primer set as described. Lane 1 is a medium only control.

FIG. 3 illustrates NASBA detection of HIV-1 infection, attempted in the presence of sCD4 and AZT.

A. HIV-$1_{IIIB}$ infection of PEA-stimulated PBMC was attempted in the presence of 0.2 (lane 2), 2.0 (lane 3), 20 (lane 4) μg/ml of sCD4. After 3 days, resulting cultures were analyzed by NASBA with the gag region primer set. Lane 1 is a medium only control; lane 5 is untreated PBMC+HIV-1$_{IIIB}$.

B. Results from NASBA analysis of attempted PBMC infection by HIV-1$_{IIIB}$ in the presence of 0.01 (lane 1), 0.1 (lane 2), 1.0 (Lane 3), or 10 (lane 4) μM AZT. Lane 5 is untreated PBMC+HIV-1$_{IIIB}$.

FIG. 4 illustrates the specificity of the HIV-1 spliced transcript primer set. Approximately 320 TCID$_{50}$ of HIV-1$_{IIIB}$ virus stock were incubated in medium at 37° C. for 30 min. Extracted nucleic acids were assayed by NASBA using either the HIV-1 spliced transcript primer set (lane 2), or the gag region primer set (lane 3). NASBA amplification of RNA from H9 cells chronically infected with HIV-1$_{IIIB}$ with spliced transcript primer set was also conducted (lane 1).

FIG. 5 illustrates detection of CEM cell infection by HIV-1$_{IIIB}$ with NASBA using the spliced transcript primer set. CEM cells are neoplastic T-cells kindly provided by Dr. D. Bolognesi of Duke University, Durham, NC.

A. CEM cells were infected with 64 (lanes 4 and 7), 32 (lanes 3 and 6) and 16 (lanes 2 and 5) TCID$_{50}$ of HIV-1$_{IIIB}$ as described. At 24 hr. (lanes 5, 6 7) and 48 hr. (lanes 2, 3 4) post infection, cultures were analyzed by NASBA with the spliced transcript primer set. Lane 1 is a medium only control.

B. CEM cells (8×10$^6$) were infected with 200 TCID$_{50}$ of HIV-1$_{IIIB}$ at 37° C. for 1 hr. and then washed with RPMI medium. Infected cells (1×10$^6$) were then treated with 0.1 (lane 1), 1.0 (lane 2), 10 (lane 3) μM AZT, or with no inhibitor (lanes 4 and 5). After 48 hr., cultures were analyzed by NASBA using the spliced primer set.

Figure 6:
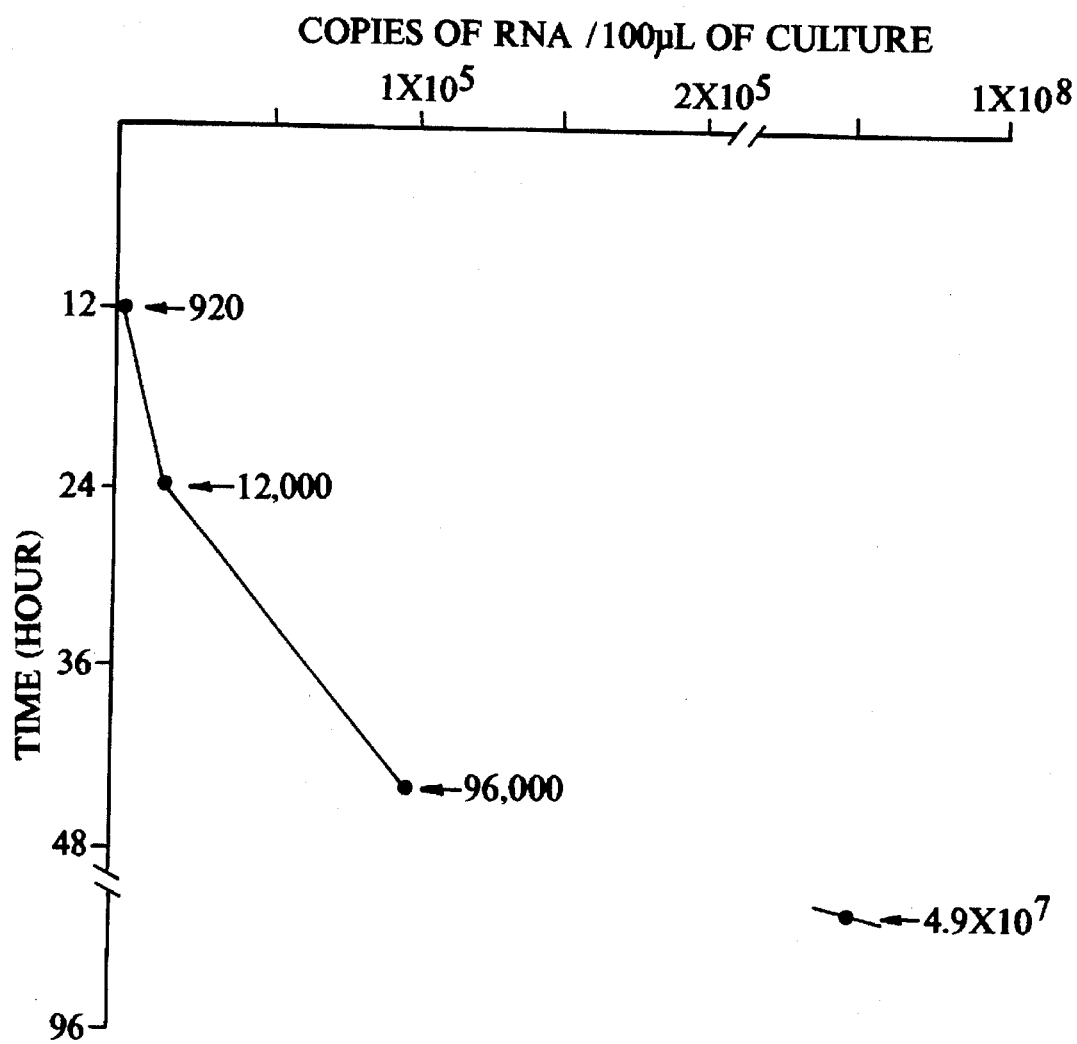

FIG. 6 depicts the infection kinetics of HIV-1 in PBMC. We were able to quantitate the actual amount of RNA synthesized during the initial phase of infection using the quantitative QT-NASBA assay (van Gemen et al., 1994). Quantitation of genomic viral RNA synthesized during the early time period minimizes the contribution of secondary infection in the measurement of infection kinetics. During the 48 to 86 hour period, there was an exponential increase in the infection kinetics, as determined by NASBA. However, similar kinds of measurements could not be made using conventional methods. For example, it has been shown that a minimum of 4 days of culturing is required before any level of infection of neoplastic T-cell lines could be detected using a standard reverse transcriptase (RT) assay (Dimitrov et al., 1993), and 5 days were required to detect the exponential expansion of infection. Clearly, a great deal of secondary infection must occur before conventional assay methods could be employed.

DETAILED DESCRIPTION OF THE EMBODIMENTS

With the present invention, using an RNA amplification technique, preferably NASBA, for the detection of spliced mRNA, certain goals have been achieved. Being able to detect infection of PBMC as early as forty-eight hours after infection eliminated the need for extended culturing and, therefore, reduced the likelihood of detecting secondary infection instead of primary infection. By minimizing secondary infection, assays performed in the presence of potential antiviral agents or inhibiting antibodies can provide relatively accurate results indicating the efficacy of the antiviral agents or antibodies in blocking or inhibiting infection. A second goal achieved is the use of peripheral blood mononuclear cells (PBMC) as the target cell in an infectivity assay. These cells are the natural cells that are the targets of infection in-vivo, and thus the assay, and the determination of antiviral or blocking activity, provides a more useful result. Also, low quantities of virus can be used in the assay, which is also more representative of infection in-vivo and provides a more useful and accurate result. The present method also provides the necessary sensitivity to detect low levels of infection.

Using the method of the invention, assays can be conducted using extremely small doses of virus. Using a small dose of virus precludes the need for a large dose of inhibitor or antiviral drug, which sometimes is toxic to cells. Moreover, using a small dose of virus, the likelihood of interaction between virus and antiviral agent is increased per virus particle. With large doses of virus, antiviral activity can be underestimated, particularly using conventionally known assays that only present sufficient sensitivity to measure secondary infection (infection by virus produced by replication after primary infection), which requires four or six days, or longer, by which time virus replication of any small proportion not inhibited could not easily be distinguished from unabated virus activity and would suggest that the antiviral agent is ineffective. Using small doses of virus and measuring virus replication at an early stage, such as within forty-eight hours after infection, the present highly sensitive assay permits a more accurate evaluation of antiviral activity.

Using small amounts of virus in infectivity assays also decreases the effect of virus heterogeneity, which is a characteristic of field as well laboratory adapted isolates. The more homogenous the virus the better the evaluation of the antiviral agent, this is particularly true with respect to evaluating antibodies that inhibit activity in certain virus strains.

Secondary infection, indicated by a virus "bloom" caused by reinfection is more easily detected. Relying on secondary infection for testing antiviral drugs, however, can lead to incorrect conclusions regarding the efficacy of the drug. For example, if an antiviral drug is 90% effective, but the assay does not detect virus until the third or fourth day after a virus bloom from secondary infection occurs, the conclusion that the drug is ineffective will result. This is because there is sufficient multiplication of the virus, even with the 10% remaining from the primary infection, to effect a late virus bloom and suggest that the drug is relatively ineffective. By detecting primary infection within the first forty-eight hours after the PBMC's are invaded by the virus, the small amount of virus resulting from the initial infection and replication can be detected and, through the amplification techniques, sufficiently quantitative analysis can be performed comparing the results of infection in the presence of the drug versus controls to demonstrate useful activity that would otherwise have been missed. Similar to testing for drug efficacy, antibodies blocking infection can be evaluated using the method of the invention.

In replication of viruses there is a splicing of genomic RNA to provide a sequence coding for the necessary proteins. Without splicing, the virus cannot replicate. If the precursor RNA can be viewed as having sections A-B-C joined together, in the course of replication A becomes spliced to C, and the junction A-C can be detected, and even quantified, using probes and known amplification methods. The probe will hybridize to the RNA from the two sections at the splice. In order to detect the small amounts of virus, and of course the small amounts of spliced RNA resulting from primary infection, prior to a virus bloom, amplification techniques are used. For example, primers that hybridize with A and with C may be used. Although they may amplify both the precursor RNA and spliced RNA, only the amplified spliced RNA will be detected and measured.

These methods permit, not only the early detection of infection and replication, but successive assays to indicate the rate of replication, which permits the evaluation of antiviral drugs and blocking antibodies, even those that may be effective in controlling reproduction of virus rather than completely eliminating them.

In the preferred embodiment, with HIV-1 and HIV-2, the junction of spliced RNA is detected for the splicing of the LTR with the tat coding regions. LTR contains a promoter and tat codes for a regulatory protein that is a transcription activator. A second junction that may be detected using a probe for the spliced region is the joining of the first approximately two-thirds of the tat gene (exon 1) and approximately the second third of the tat gene (exon 2). Between these two regions in the precursor lies an intron, which is eliminated in preparation for virus replication. The same junction sequence as in the tat sequence is found in a junction in the sequence coding for the rev protein, which hybridizes with the same probe.

Like the HIV retroviruses, HTLV-I and HTLV-II also produce spliced RNA during replication, and the junction in which the LTR region becomes spliced to the tax gene provides a junction for detection with a probe. The tax gene is equivalent to the tat gene of HIV in function.

This method permits the use of peripheral blood mononuclear cells rather than the usual transformed cell lines, such as the H9 T-cell line. Using PBMC from normal donors results in a system for assessing vital infection that is reflective of what happens in a patient at the time of infection. By contrast, invasion and propagation in immortalized cells normally requires selection for the phenotype that is better able to survive and invade the transformed T-cells. PBMC provide a true in-vivo target and measurement of infection in a more biologically relevant system than transformed T-cell lines.

EXAMPLES

Infection Assays

Two different protocols were used in the assays to test antiviral agents, testing their ability to inhibit infection of PBMC with HIV-1. In protocol 1, virus was pre-incubated with either soluble CD4 (sCD4) or neutralizing antibodies prior to infection of PBMC. In protocol 2, PBMC were infected with HIV-1$_{IIIB}$ and then treated with AZT.

Cells and Virus

Peripheral blood mononuclear cells (PBMC) from HIV-1 seronegative buffy coat (Red Cross, Rockville, Md.) were harvested by banding on Ficoll-Hypaque and cultured for 48 hr. in RPMI containing 20% fetal calf serum, 250 units penicillin/streptomycin, 2 mML-glutamine, 10% interleukin-2 (IL-2; Boehringer Mannheim) and 5 µg/ml PHA-P (Burroughs-Wellcome). The cells were then washed in RPMI and used for infection assays as described below.

Uninfected CEM and chronically-infected Molt3/HIV-1$_{IIIB}$ cells were maintained in RPMI medium supplemented with 10% fetal bovine serum, 1 mM glutamine, 100 units/ml penicillin and 100 µg/µl streptomycin. Virus stock for infection assays was prepared by culturing Molt3/HIV-1$_{IIIB}$ cells in fresh medium. The cell-free supernatant was collected after 24 hr., filtered and stored in aliquots of 1 ml at –70° C. prior to use. The virus stock was titered with PBMC as target cells to determine the median tissue culture infectious dose (TCID$_{50}$) based on the amount of p24 antigen produced in culture (using the Organon Teknika antigen capture assay) after 7 days of infection.

Protocol 1

Virus stocks (200 µl) were mixed with antibodies and with sCD4 and incubated in wet ice for 60 min., and at room temperature for an additional 15 min. One hundred microliters of medium containing PHA-stimulated PBMC (10$^7$/ml) were added to each tube and incubated at 37° C. for 60 min. The cells were spun down and washed with 5 ml RPMI medium to remove unadsorbed virus and the inhibitor. The cells were then plated onto a 24-well plate at a density of 10$^6$cells/ml in RPMI medium containing 20% fetal calf serum, 250 units penicillin/streptomycin, 2 mM L-glutamine and 10% native human IL-2. In the case of soluble CD4, the inhibitor was present during the entire course of infection. One hundred microliters of these cultures were harvested at different days after infection and subjected to RNA extraction as described below.

Protocol 2

In this protocol, PBMC (1×10$^6$ cells) in 300 µl of RPMI medium were mixed with different doses of HIV-1$_{IIIB}$ and incubated at 37° C. for 60 min. After removing unbound virions, the cells were washed in RPMI and plated into a 24-well plate at a density of 1×10$^6$ cells/ml in RPMI containing 10% IL-2. Different concentrations of AZT prepared in PBS was added to each well and the cells were cultured for 3 days. One hundred microliters of culture medium containing 1×10$^5$ cells were subjected to RNA extraction as described below.

Analysis of the production of spliced HIV-1 transcript was achieved in acutely infected CEM cells. Briefly, CEM cells (8×10$^6$) were infected with HIV-1$_{IIIB}$ virus (200 TCID$_{50}$) in 500 µl RPMI medium for 60 min. at 37° C. Cells were then washed with 10 ml of RPMI medium distributed in 25 cm$^2$ flasks, each containing 1×10$^6$ cells in 4 ml medium (2.5×10$^5$ cells/ml). Different concentrations of AZT in PBS were then added to each flask and the cells were cultured for 3 days. One hundred microliters of culture were removed for nucleic acid extraction and NASBA analysis as described below.

NASBA Reactions

Nucleic acids were extracted from PBMC cultures by the technique of Boom et al. (1990). NASBA reactions were conducted as described by van Gemen et al. (1993). The reactions involved 2–5 µl of the extracted nucleic acid solution in a total reaction volume of 25 µl, which was made from 40 mM Tris, pH 8.5, 12 mM MgCl2, 42 mM KCl, 5 mM DTT, 15% v/v DMSO, and 1 mM each dNTP, 2 mM each NTP, 0.1 µg/µl BSA, 0.1 unit of RNase H, 40 units of T7 RNA polymerase, 8 units of AMV-reverse transcriptase, and 0.2 µM of each primer. Amplification of the HIV-1 gag site (Kievits et al., 1991) was achieved with the following primer set: P1, 5'AAT TCT AAT ACG ACT CAC TAT AGG GAT TGC CTC TCT GCA TCA TTA 3' (SEQ. ID. NO:1) ; and P2, 5'AGC ATT GGG ACC AGC GGC TA 3' (SEQ. ID. NO:2). Amplification of the spliced HIV-1 tat transcript required the development of a new primer set, which was derived from the sequence of the HXB2 clone of HIV-1 (Myers et al., 1992): P1, 5'AAT TCT AAT ACG ACT CAC TAT AGG GCC AAG GAT CCG TTC ACT AAT CGA ATG 3' (SEQ. ID. NO:3); and P2 5'TCA GAA CAG TCA GAC TCA TCA AGC TTC 3' (SEQ. ID. NO:4). Underlined sequences represent the portions of the primer that encode the T7 RNA polymerase promoter. Reactions were conducted at 41° C. for 90 min. Reaction products were stored at −20° C. until analyzed (see below).

Hybridization Analysis of NASBA Reaction Products

NASBA products were analyzed through the use of a hybridization detection procedure. Briefly, 5–7.5 µl of NASBA reaction product were electrophoresed through a 2.0% agarose gel, and transferred with a VacuGene XL vacuum blotting apparatus (Pharmacia, Piscataway, N.J.) to a nylon membrane using 2×SSC (1×SSC is 150 mM sodium chloride [NaCl], 70 mM sodium citrate, pH 7.0) as the transfer solution. Once immobilized on the nylon membrane, this blot was hybridized with a a $^{32}$P labeled oligonucleotide probe in a solution of 5×SSC, 20 mM sodium phosphate, pH 7.0, 7% sodium dodecyl sulfate (SDS), and 10×Denhardt's solution at 50°–55° C. for 16–24 hr. Blots were washed with 3×SSC, 1.0% SDS 50°–55° C., and exposed to film in autoradiography for an appropriate time period. The sequence of the probe used for the analysis of the gag region target was 5'TAG AAG AAA TGA TGA CAG CAT GTC AGT GA 3'(SEQ. ID. NO:5); and, for the spliced transcript target, 5'TCT ATC AAA GCA ACC CAC CTC CCA 3'(SEQ. ID. NO:6) (the italics sequence represents the portion of the probe which hybridizes to the upstream sequence adjacent to the splice junction; the remaining portion of the probe is specific for the downstream sequence adjacent to the splice junction). Densitometric measurements of resulting autoradiographs were conducted with the LKB Ultroscan XL Enhanced Laser Densitometer.

Results

Virus Dose Optimization:

Initially, the minimal virus dose that would lead to productive infection of the PBMC target cells was determined. This was needed to establish that any virus RNA detected by NASBA after infection was due only to the formation of new genome molecules. Therefore, separate wells of PHA-stimulated PBMC ($10^6$ cells/ml/well) were infected with 16.0, 4.0, 2.0, and 1.0 TCID$_{50}$ doses of the HIV-1IIIB isolate. After 3 days, nucleic acids were extracted from 100 µl of culture and then analyzed by NASBA with the gag region primer set. Reaction products were analyzed by the hybridization method described. FIG. 1A shows that all doses of virus used in this experiment lead to productive infection of PBMC. As expected, inherent variability in susceptibility of infection was found to exist between different batches of PBMC. However, it was consistently observed that 4.0 TCID$_{50}$ of virus led to productive infection of all batches of PBMC tested. Therefore, 4.0 TCID$_{50}$ was used as the infectious dose in all subsequent experiments.

In order to determine the earliest time point at which the infection of PBMC can be detected, PBMC infected with 4.0 TCID$_{50}$ were analyzed by NASBA using the gag region primer set at 24 hr intervals after initiation of infection. FIG. 1B shows that, although under these conditions no viral genome can be detected by NASBA at 0 and 24 hr, HIV-1 RNA was readily detected at 48 and 72 hr post-infection, suggesting that the detected RNA represents newly formed viral genome. Although infection of PBMC was detectable by NASBA as early as 48 hr post infection, the 72 hr time point became the standard assay point. This would prevent a potential overestimation of the inhibitory effect of a given antiviral agent, through premature evaluation of the infection status of a culture.

Use of NASBA to Study Virus Neutralization with Antibodies:

Detection of HIV-1 genomic RNA by NASBA was used to determine the effect of neutralizing antibodies on the infection of PBMC by the HIV-1$_{IIIB}$ isolate. A well characterized HIV-1 antibody positive human serum (PS12), and a monoclonal antibody specific for the V3 domain of the HIV-1$_{IIIB}$ gp120 envelope molecule (M77), were selected for this study. These two antibodies neutralize HIV-1 by two different mechanisms (Pal et al., 1992). Four TCID$_{50}$ of HIV-1$_{IIIB}$ were preincubated with 1:20, 1:200, and 1:2,000 dilutions of either PS12 or M77, and then used to infect PHA-stimulated PBMC. Extracts from each of these cultures were analyzed by NASBA with the gag region primer set. Percent neutralization was measured by densitometric analysis of the autoradiogram represented in FIG. 2A. The signal intensity obtained from each of the serum/antibody treated infection samples was compared to the signal intensity obtained from PBMC infected in the absence of antibody. As summarized in Table 1, infection was almost completely inhibited in the presence of either antibody at 1:20 dilutions, whereas only 21% and 12% inhibition was noted at the 1:2,000 dilutions of M77 and PS12, respectively. As expected, normal human serum had no effect on HIV-1 infection (FIG. 2B).

Effects of sCD4 and AZT on HIV-1 Infection of PBMC:

The NASBA-based infection assay was also used to evaluate the inhibitory effect of antiviral agents on HIV-1 infection. Both soluble CD4 (sCD4) and AZT were selected for such studies since they are also potent inhibitors of HIV-1 infection. PHA-stimulated PBMC were infected with 4.0 TCID$_{50}$ of HIV-1$_{IIIB}$ in the presence of different concentrations of either sCD4 or AZT, and were analyzed by NASBA with the gag region primer set. The percentage of inhibition was determined by densitometric analysis of the resulting autoradiogram (FIG. 3). As summarized in Table 1, 20 µg/ml of sCD4 completely inhibited infection of PBMC by HIV-1$_{IIIB}$, whereas approximately 86% inhibition was noted at 0.2 µg/ml. As expected, AZT was shown to be a very effective inhibitor of HIV-1 infection, with as little as 0.01 µM AZT causing 93% inhibition.

Use of NASBA to detect spliced HIV-1 transcript produced during primary in vitro infection:

After establishing the utility of NASBA as an end point assay for determining HIV-1 infection, effort was directed to adapting NASBA for the detection of spliced HIV-1 transcript. Specifically, the splice junction between the first and second exons of the tat transcript was targeted. This species of HIV-1 mRNA is only detectable within cells that are undergoing virus replication (Ratner, 1993). The NASBA primers used in these studies were designed to amplify a region initiating 39 bases upstream from the splice junction site and extending to a position 107 bases downstream from the junction. The 24 base oligonucleotide probe used to detect the amplified product is specific for the splice junction region (i.e., 12 bases upstream and 12 bases downstream from the splice junction). In the absence of a splicing event, the two primers are separated by more than 2.3 kb in the genomic RNA molecule, and therefore would not be amplified by NASBA under the conditions being used. Further, the probe used to detect the product of this amplification reaction would be nonfunctional because it would be divided in half and separated by the same distance.

Prior to the use of the spliced primer set in the detection of virus infection, initial characterization was performed to examine the specificity of the primer set. RNA was extracted from a virus stock of HIV-1$_{IIIB}$, that was preincubated in medium for 30 min at 37°. This RNA was then amplified by NASBA using the spliced transcript primer set, as well as the gag region primer set. As expected, virus stock RNA was amplified by the gag region primers (FIG. 4, lane 3), whereas no product was detected when the spliced transcript primer set was used (FIG. 4, lane 2). As a control, RNA extracted from H9 cells chronically infected with HIV-1$_{IIIB}$ was amplified with the spliced transcript primer set (FIG. 4, lane 1). The sensitivity of the spliced transcript primer set was determined by analyzing the extracted RNA from cocultures of a different number of H9 cells chronically infected with HIV-1$_{IIIB}$ and $10^5$ uninfected CEM cells. These experiments indicated that this primer set could be used to detect between 1 and 10 infected cells, against a background of 10,000 uninfected cells.

Figure 5B:
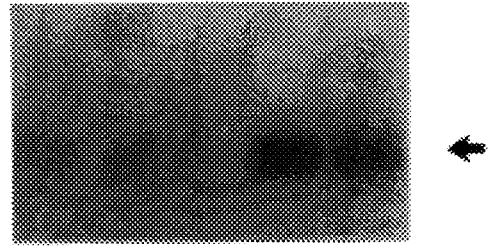

NASBA, with the spliced transcript primer set, was used to assay primary HIV-1 infection. CEM cells were infected with 16, 32, and 64 TCID$_{50}$ of HIV-1$_{IIIB}$, and resulting cultures were assayed at different times after infection. At higher doses of virus (32 and 64 TCID$_{50}$) spliced transcript could be detected as early as 24 hr, whereas 48 hr were required for a lower dose (16 TCID$_{50}$; FIG. 5A). Further, the spliced transcript primer set could be used to detect the inhibition of HIV-1 infection by AZT in a dose dependent manner (FIG. 5B). CEM cells that were acutely infected by HIV-1$_{IIIB}$ were treated with different doses of AZT. As with the gag region primer set, the spliced transcript primer set could also be used to monitor the inhibition of infection by AZT. However, in this case inhibition was being monitored through the detection of a specific molecular intermediate; the spliced mRNA transcript. The percent inhibition by AZT as determined with the spliced transcript primer is summarized in Table 2.

TABLE 1

Percentage of HIV-1$_{IIIB}$ Infection Neutralization/Inhibition as Determined by Densitometric Analysis of NASBA Reaction Products

| Antibody | Percent Neutralization | | Percent Inhibition |
|---|---|---|---|
| HIV-1$_{IIIB}$ + 1/20 M77 | >98% | sCD4: | |
| HIV-1$_{IIIB}$ + 1/200 M77 | 91% | HIV-1$_{IIIB}$ + 0.2 ug/ml sCD4 | 86% |
| HIV-1$_{IIIB}$ + 1/2000 M77 | 21% | HIV-1$_{IIIB}$ + 2.0 ug/ml sCD4 | >98% |
| | | HIV-1$_{IIIB}$ + 20 ug/ml sCD4 | >98% |
| HIV-1$_{IIIB}$ + 1/20 PS12 | 96% | | |
| IV-1$_{IIIB}$ + 1/200 PS12 | 89% | AZT: | |
| IV-1$_{IIIB}$ + 1/2000 PS12 | 12% | HIV-1$_{IIIB}$ + 0.01 μM AZT | 93% |
| | | HIV-1$_{IIIB}$ + 0.1 μM AZT | >98% |
| | | HIV-1$_{IIIB}$ + 1.0 μm AZT | >98% |
| | | HIV-1$_{IIIB}$ + 10 μM AZT | >98% |

TABLE 2

Percentage of inhibition of HIV-1$_{IIIB}$ infection of CEM cells as Determined by NASBA with the Spliced Transcript Primer Set

| DOSE OF AZT | % INHIBITION |
|---|---|
| 0.1 μm AZT | 75% |
| 1.0 μm AZT | >85% |
| 10 μm AZT | >85% |

We claim:

1. A method for determining human immunodeficiency virus (HIV) replication resulting from primary infection of human cells using an RNA amplification method, comprising providing a sample of human peripheral blood lymphocytes, extracting the nucleic acid from the peripheral blood lymphocytes, adding amplification primers that hybridize with exon 1 and exon 2 of a spliced tat gene RNA segment, amplifying RNA comprising exon 1 and exon 2, adding a probe that will hybridize with the junction of exon 1 and exon 2 in a spliced RNA tat mRNA, and detecting the hybridization of said probe with said spliced RNA, wherein a positive result is obtained when hybridization occurs and indicates HIV replication.

2. The method of claim 1, wherein the probe is labeled with a detectable label selected from the group consisting of an enzyme, a sol particle and a radionuclide.

3. The method of claim 1, wherein the probe is detected using a labeled, complementary nucleic acid sequence that hybridizes specifically to the probe.

4. The method of claim 1, wherein the infection is detected within forty-eight hours of primary infection in-vitro.

5. A method for evaluating an antiviral agent or inhibiting antibody comprising introducing an antiviral agent or inhibiting antibody into serum containing human peripheral blood mononuclear cells and determining HIV replication by the method of claim 1.

6. The method of claim 5, wherein the antiviral agent or inhibiting antibody is evaluated by determining HIV replication within approximately the first forty-eight hours after infection in-vitro.

7. The method of claim 6, wherein the efficacy of the antiviral agent or inhibiting antibody is determined by obtaining the percent of inhibition of HIV infection.

8. The method of claim 1, wherein the peripheral blood lymphocytes are peripheral blood mononuclear cells.

* * * * *